(12) United States Patent
Hubbard et al.

(10) Patent No.: US 8,892,394 B1
(45) Date of Patent: *Nov. 18, 2014

(54) SYSTEM AND METHOD FOR RACE PARTICIPANT TRACKING AND REPORTING OF ASSOCIATED DATA

(71) Applicants: Jason R. Hubbard, Brentwood, TN (US); Floyed Jeffries Duncan, Brentwood, TN (US)

(72) Inventors: Jason R. Hubbard, Brentwood, TN (US); Floyed Jeffries Duncan, Brentwood, TN (US)

( * ) Notice: Subject to any disclaimer, the term of this patent is extended or adjusted under 35 U.S.C. 154(b) by 91 days.

This patent is subject to a terminal disclaimer.

(21) Appl. No.: 13/799,083

(22) Filed: Mar. 13, 2013

Related U.S. Application Data

(63) Continuation of application No. 12/950,348, filed on Nov. 19, 2010, now Pat. No. 8,473,242, and a continuation-in-part of application No. 12/798,680, filed on Apr. 12, 2010, now abandoned.

(51) Int. Cl.
*A61B 5/00* (2006.01)
*G06F 3/0481* (2013.01)
*A61B 5/11* (2006.01)

(52) U.S. Cl.
CPC ............ *G06F 3/0481* (2013.01); *A61B 5/0022* (2013.01); *A61B 5/1112* (2013.01)
USPC ............................ 702/150; 702/182; 363/113

(58) Field of Classification Search
CPC ........................... A61B 5/1112; A61B 5/0022
USPC .................................... 702/150, 182; 368/113
See application file for complete search history.

(56) References Cited

U.S. PATENT DOCUMENTS

| | | | |
|---|---|---|---|
| 5,731,788 | A | 3/1998 | Reeds |
| 6,013,007 | A | 1/2000 | Root et al. |
| 6,020,851 | A | 2/2000 | Busack |
| 6,148,262 | A | 11/2000 | Fry |
| 6,463,385 | B1 | 10/2002 | Fry |
| 6,662,016 | B1 | 12/2003 | Buckham et al. |
| 6,744,403 | B2 | 6/2004 | Milnes et al. |
| 7,136,747 | B2 | 11/2006 | Raney |
| 7,158,912 | B2 | 1/2007 | Vock et al. |
| 7,233,795 | B1 | 6/2007 | Ryden |
| 7,474,896 | B2 | 1/2009 | Mohi et al. |
| 7,532,977 | B2 | 5/2009 | Chen |
| 7,534,206 | B1 | 5/2009 | Lovitt et al. |
| 2004/0013045 | A1 | 1/2004 | Setler |
| 2004/0078208 | A1 | 4/2004 | Burwell |
| 2006/0016173 | A1 | 1/2006 | Dhaliwal |
| 2008/0036587 | A1 | 2/2008 | Meinzen et al. |
| 2009/0258710 | A1 | 10/2009 | Quatrochi et al. |

*Primary Examiner* — Corbett B Coburn
(74) *Attorney, Agent, or Firm* — Waddey Patterson; I. C. Waddey, Jr.; Gary L. Montle

(57) ABSTRACT

A system and method are provided for tracking race participants via a Global Positioning System, providing feedback in substantially real time to the race participant, and optionally to other remote individuals via web publication at the user's preference. The feedback includes graphical and tabular presentation of such information as geographic position, race route, current race performance metrics, projection of future milestone and final race performance, projected position at a given time, projected time to a given position, relative performance to historical participants, to personal historical performance and to other members of the current race that are being tracked in aggregate or by demographic or otherwise subdivided.

22 Claims, 2 Drawing Sheets

SYSTEM AND METHOD FOR RACE PARTICIPANT TRACKING AND REPORTING OF ASSOCIATED DATA

CROSS-REFERENCES TO RELATED APPLICATIONS

This application is a continuation of co-pending U.S. patent application Ser. No. 12/950,348, filed on Nov. 19, 2010, which is a continuation-in-part of U.S. patent application Ser. No. 12/798,680 (since abandoned), filed on Apr. 12, 2010.

A portion of the disclosure of this patent document contains material that is subject to copyright protection. The copyright owner has no objection to the reproduction of the patent document or the patent disclosure, as it appears in the U.S. Patent and Trademark Office patent file or records, but otherwise reserves all copyright rights whatsoever.

STATEMENT REGARDING FEDERALLY SPONSORED RESEARCH OR DEVELOPMENT

Not Applicable

REFERENCE TO SEQUENCE LISTING OR COMPUTER PROGRAM LISTING APPENDIX

Not Applicable

BACKGROUND OF THE INVENTION

The present invention relates generally to the realm of racing over a broad geographical area (relative to the resolution of Wireless Positioning Technology) such as cross country or marathon running, sailing races or regattas, biking, road rallies and the like. More particularly, the present invention relates to a system and method for obtaining information in substantially real time from a race participant and generating and providing feedback associated with the obtained information.

There exists an unmet opportunity to provide the race participant with valuable feedback through the interpretation of data collected by for example wireless positioning technology and ancillary data that is readily available prior to and during the race. Such ancillary data might include information such as biometric data, local equipment data, the race route, positions of other participants of the race, etc. Other useful ancillary data might include historical performance of the participant or other participants potentially of notoriety who have raced the same course. Such data could be utilized either individually or in aggregate.

As is typical of racing enthusiasts, technology is being utilized in increasing innovative manners to monitor personal information and performance during a race and training. Typically however this has been limited to locally collected and communicated data such as heart rate, pedometer-derived pace and strides, and the local presentation of GPS data. The opportunity to capture and provide a more expansive and useful set of data and information based on the interpretation of this data will be appreciated by race participants.

Systems and methods as presently known in the art generally fail to provide feedback to the participant of the race or directly to observers of the race which may be used to determine the position of the user along a race route in substantially real time and remotely accessible. Where positions or locations are currently generated, these are generally obtained through triangulation of a number of devices or in relation to at least one fixed ground-based wireless network structure having a known geographic location. It would be desirable to obtain positioning information associated with a race participant and track the race participant with respect to a predetermined route, and optionally with respect to other actual or virtual participants.

BRIEF SUMMARY OF THE INVENTION

Various systems and methods are described herein in accordance with embodiments of the present invention wherein a participant in a race or otherwise practicing/training for a race is tracked via a local smart device providing a plurality of performance metrics.

In an embodiment, a system and method of tracking a participant in an event includes a local device such as a mobile communications device. Real time performance data associated with the participant is obtained at or by the device. Route data associated with the event is obtained at the local device, either by manual entry from a user or by downloading from a remote server. A graphical map interface is generated on a user display of the local device based at least in part on the route data. One or more performance metrics are displayed on the user display based on the real time performance data. A position of the participant is determined from the real time performance data and displayed in association with the generated graphical map interface.

In another embodiment, a system and method in accordance with the present invention include a portable communications device which obtains real time performance data associated with a participant in an event such as for example a race and further obtains route data associated with the event. A graphical map interface is generated on a user display of the local device based at least in part on the route data. A position of the participant is determined from the real time performance data. Historical performance data associated with the participant is further obtained at the device, the position of the participant is displayed in association with the generated graphical map interface and further relative to a corresponding position associated with the historical performance data.

DETAILED DESCRIPTION OF THE INVENTION

Figure 1:
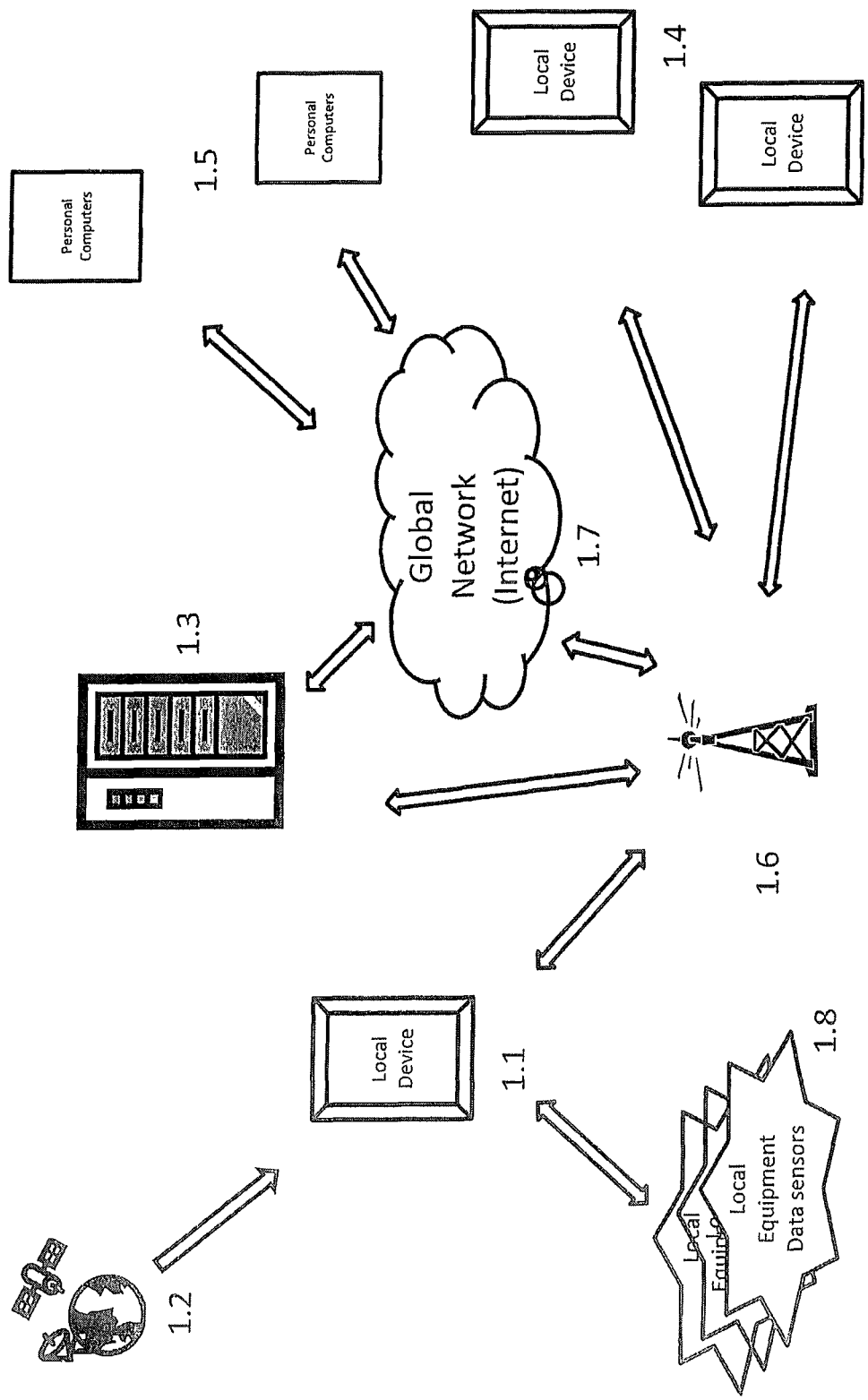
FIG. 1 is a block diagram representing an embodiment of a system in accordance with the present invention.

Throughout the specification and claims, the following terms take at least the meanings explicitly associated herein, unless the context dictates otherwise. The meanings identified below do not necessarily limit the terms, but merely provide illustrative examples for the terms. The meaning of "a," "an," and "the" may include plural references, and the meaning of "in" may include "in" and "on." The phrase "in one embodiment," as used herein does not necessarily refer to the same embodiment, although it may.

The term "Wireless Positioning Technology" as used herein may generally refer to a government maintained satellite GPS (Global Positioning System) system as presently known in the art, but may without limitation further include any service available on a local or global basis through which positions of race participants can be determined substantially in real time for use in the various systems and methods described herein.

The term "Biometric Data" as used herein may generally include any data representative of physical measurements that can be captured by or delivered to a local device about the race participant(s) and/or their equipment. Such measurement information might for example include heart rate, pulse rate, respiratory rate, body temperature and a stride/pace of the participant.

The term "Local Device(s)" as used herein may generally refer to a commercially available portable computing device, communications device or otherwise "smart" system having a microprocessor, display and one or more associated communications systems or portals. Such devices may include for example PDA devices, cell phones and other such systems specifically including but not limited to brands such as Apple's iPhone and Research in Motion's Blackberry devices. The local device used by the race participant may be GPS enabled or otherwise capable of determining a location of the local device or data representative of the location of the local device.

The term "Local Equipment Data" as used herein may include any physical measurements that can be captured by or delivered to the local device about the race participant's equipment. Such measurement information might include but not be limited to operating temperatures, pressures, speeds, accelerometer readings, levels of consumables and the like.

The term "Server" as used herein may refer to one or more remote computing, communications and storage devices accessible by the local devices and capable of receiving, storing, manipulating and transmitting data to and from users and observers during a race as well as providing access to data in its storage. The server will provide adequate security to ensure servicing only communications with adequate authority.

The term "Virtual Racer" as used herein may generally refer to a set of data representing a racer that is not physically performing or competing in a race associated with the present actual race participant(s). This data may for example represent a racer of notoriety such as a previous winner, or a theoretical racer that might be defined to provide a desired pace. Users and observers may in various embodiments of the present invention have the ability to enable "virtual" racers on their displays and track them relative to "actual" participants.

In various embodiments as described herein, the system includes a software program module such as an iPhone application which is developed and made available via online download to implement the envisioned functionality in a local device. The envisioned functionality may in various embodiments further generally relate to one or more runners, or more particularly to Marathon runners.

Referring to FIG. 1, a system in accordance with the present invention may generally be described. A local device (1.1) may be located on or otherwise positioned in association with a race participant. This device may be in or otherwise have the capability of routine reception of GPS satellites (1.2) or other wireless positioning technology capable of determining its location. The local device obtains or calculates via the wireless positioning technology and/or local equipment data sensors (1.8) real time performance data such as for example position, speed, pace, temperature, heartbeat, etc. This real time performance data may then optionally be displayed via characters or graphics on the local device display. In addition the data may in various embodiments periodically be communicated via a wireless link (1.6), such as a cell data network, optionally thru a global network (1.7) and to a remote server (1.3). The server will subsequently provide access to other users who have proper credentials the ability to access the data available through for example the Internet or other appropriate data network (1.7). This will be accomplished by other users (observers) displaying similar graphics or textual information as available to the race participant either on their local devices (1.4) or via the web on a personal computer client (1.5).

Figure 2:
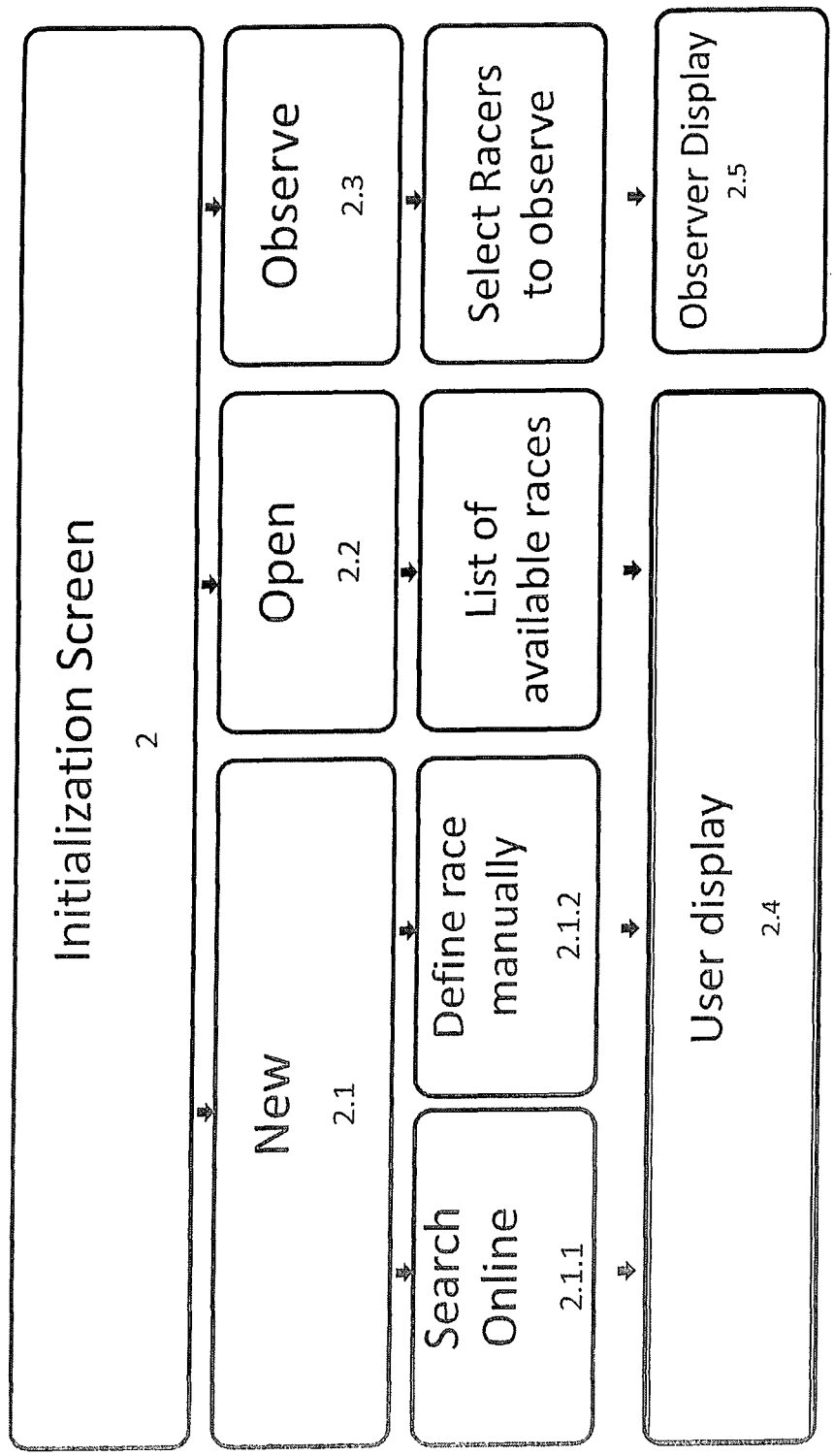
FIG. 2 is a flowchart representing an embodiment of a method of operation in accordance with a system of the present invention.

With further reference to FIG. 2, in an embodiment of the present invention, after downloading, installing and activating the application the user may be presented with three options for usage.

The first option "NEW" (referenced as 2.1) allows the user to add a route not previously stored in the device.

This selection in turn allows the user two subsequent options shown as "Search Online" (2.1.1) and "Define race manually" (2.1.2).

If "Search Online" 2.1.1 is selected the user will be provided assistance via a configurable search screen to search available routes for download and the ability to purchase and download the selected route.

If the "Define race manually" option 2.1.2 is selected, the user is provided a graphical map interface to locate for example an event starting point, intermediate turns or via points, an event distance, an ending or finish point, customized milestone locations, etc., which would define a custom route to be run. That route may then be saved to the device and in a users account on the server.

In either case, the user may then be presented a graphical map of the race selected with the current GPS location overlaid or otherwise superimposed with the graphical map, and a user defined selection of the available metrics shown on a User Display (2.4) as further described below.

The second option shown in FIG. 2 is designated "Open" (2.2). Selecting this option allows the user to view a list of races previously downloaded or manually defined. The user may then select the race desired and be presented a graphical user interface containing a map of the race (route) selected with the current GPS location overlaid or otherwise superimposed on the map, and a user defined selection of the available metrics shown on the User Display (2.4).

The User Display may in various embodiments provide the user an ability to pan, zoom and auto track on the map. Options may be made available to modify the metrics being shown and perform other administrative tasks such as enabling/disabling observers, allowing public observation, setting passwords, defining reporting frequencies, etc. Additional options may be provided for enabling external devices for ancillary data collection such as heart/respiration monitors or temperature/humidity monitors. The racer (participant) may also be able to enable observation of other race participants on his local display. The ability to start and or stop the race either manually or automatically based on GPS location may further be provided.

In various embodiments a plurality of metrics which may be displayed in substantially real time during the race (real time performance data) via the User Display of an associated local device may include but are not limited to any available or displayable number of measures such as for example: a current speed; a current pace or stride (in the example of a runner); an average speed over a past specified period; an average speed since the beginning of the race; a current speed represented as for example a percent of an average speed as mentioned above; heart rate; respiration rate; body temperature; other biometric metrics as might be externally measured and accessible by the local device; ambient temperature; calories burn rate and/or total calories burned over a specified period; local equipment data; a current position in the race relative to reference data; and various subsets of these measures based on age, gender, elite participants, or other distinguishing criteria.

Reference data as mentioned above may in various embodiments include for example real time performance data associated with other actual participants that are currently being tracked, historical performance data of the participant or of other participants, predetermined or otherwise manually derived theoretical performance data, or a consolidation of a plurality of such data from this or a similar race.

In various embodiments, graphical representations of the information available may be provided on the user display of the local device, and might include without limitation a graphical street map view or satellite image view of the course or a part thereof, an overhead (birds-eye) view with the route superimposed thereon, and the same views with the location of the participant and/or other participants and/or any virtual racers superimposed thereon.

Information (data metrics) and associated graphical representations as previously described may also be provided to authorized observers of the race (having the appropriate credentials), and may be done so simultaneously for multiple participants.

The server may in various embodiments of the present invention have the capability of archiving, summarizing, trending and providing query capability of the data communicated to it. This may allow such downstream analysis as training progress, comparisons to benchmarks, recall of previous performance or various ad hoc queries to be performed as may be desired by the user. Proper credentials may generally be required to access said data.

The third option from the main screen designated "Observe" (2.3) may be utilized by observers and allows the same client software to be utilized by both the race participant(s) and race observers. When this option (2.3) is selected the observer may be required to enter an identifier or other user ID (typically an email address) of the race participant(s) they wish to monitor, their own ID (typically an email address) and an associated security code provided to them by the race participant (if required). Once a race is identified by the first participant, the observer may also be able to select other participants from that race who have made their data feed public or who have otherwise provided permission. The observer may then be presented a graphical map of the race selected with the current GPS location overlaid and a user defined selection of available metrics on an Observer Display (2.5). Screen 2.5 may generally be similar to 2.4, but without some of the race participant-specific options such as for example enabling external devices for ancillary data collection, enabling particular observers, etc.

In both 2.4 and 2.5 screens a "Virtual racer" can also be enabled for observation (if available) from the server.

This virtual racer may represent the performance of an historical or theoretical race participant and may be for example the previous year's winner, a previous performance of the participant, a theoretical performance to pace the runner, etc. The virtual racer would be plotted, overlaid or otherwise superimposed on the map in a method similar to that previously described with reference to actual race participants.

Periodically, at a predetermined frequency or one that is defined by the race participant, the current location and biometric data and local equipment data will be communicated wirelessly to the central server where the information can be archived, consolidated and viewed via the server over the Internet. The server archives this data for later retrieval with proper credentials and provides access to the data in substantially real time to observers. The server may also host available maps of planned race routes and virtual participants' historical performance data which will be accessed on demand as described above. The server may further have the ability to maintain multiple races run on the same route at different times, by different runners/virtual racers and to provide graphical and tabular comparisons of the same for display and analysis.

In various embodiments, the predetermined race locations and routes may be used not only for display but also in combination with the obtained real time information to predict and/or extrapolate to future events such as time and elapsed time for arrival at an intermediate point or at the end of the race.

In various embodiments, the system may be able to compare the various metrics mentioned above to predetermined benchmark values that may be from the participant's own history, custom developed benchmarks, historical benchmarks from other race participants or any combination of the aforementioned.

In various embodiments, the system may accept and respond to inquiries from an observer as to the projected location at a given or incremental time, or conversely, project the time or incremental time of arrival to a given location which is either predetermined along the route length or selectable by the observer, such as for example a location of the observer.

The server may further be effective to consolidate data with that of other race participants which are utilizing the program, and optionally with other historical, theoretical or user defined profiles, to calculate and present additional information such as for example a graphical location of individuals or average location of other participants, or a percentage position relative to the other participants. The percentage position may be relative to another participant in a particular gender group, in an age and gender group, relative to other participants adjusted for age and gender, relative to predetermined benchmark performances, relative to elite performing groups, etc.

Thus, although there have been described particular embodiments of the present invention of a new and useful System and Method for race Participant Tracking and Reporting of Associated Data, it is not intended that such references be construed as limitations upon the scope of this invention except as set forth in the following claims.

What is claimed is:

1. A method comprising:
    enabling an observer of an event having at least one participant to select the event via a graphical user interface on a display unit for a user computing device;
    generating a graphical map interface on the display unit, the map interface displaying a predetermined route for the event;
    obtaining a real time position of the participant along the route using a position sensing device and performance data associated with the participant and the event, and displaying the position in association with the route displayed on the graphical map interface;
    enabling the observer to generate an inquiry as to the elapsed time or time of arrival for the participant with respect to an arbitrary real time position of the observer at an intermediate point along the race route;
    comparing the real time performance data for the participant to the route data and predicting the elapsed time or time of arrival at the real time position of the observer for the participant with respect to said inquiry; and displaying the predicted elapsed time or time of arrival at the real time position of the observer for the participant on the display unit.

2. The method of claim 1, further comprising enabling the observer to select a participant from a plurality of participants associated with the event via the graphical user interface.

3. The method of claim 2, further comprising obtaining historical performance data associated with the selected participant and displaying the real time position of the participant relative to a corresponding position associated with the historical performance data.

4. The method of claim 2, further comprising displaying the position of a first participant selected by the observer relative to corresponding positions associated with the real time performance data for additional selected participants.

5. The method of claim 2, further comprising obtaining historical performance data associated with the selected participant and displaying real time performance metrics for the participant relative to corresponding performance metrics associated with the historical performance data.

6. The method of claim 2, the selected participant comprising an actual participant in the event, the method further comprising obtaining historical performance data associated with one or more previous participants in the event and displaying the position of the actual participant relative to corresponding positions associated with the historical performance data for the previous participants.

7. The method of claim 2, the selected participant comprising an actual participant in the event, the method further comprising obtaining theoretical performance data associated with one or more virtual participants in the event and displaying the position of the actual participant relative to corresponding positions associated with the theoretical performance data for the virtual participants.

8. The method of claim 1, the performance data for the participant comprising positioning data obtained via a GPS system.

9. The method of claim 8, the performance data for the participant further comprising one or more of biometric measurement data and local equipment measurement data.

10. The method of claim 1, further comprising a step of comparing the performance data for the participant to predetermined benchmark values.

11. A portable device having a microprocessor, a display unit, a communications port and a software program module embodied therein, the program module effective when executed by the microprocessor to direct the performance of:
enabling an observer of an event having at least one participant to select the event via a graphical user interface on the display unit;
generating a graphical map interface on the display unit, the map interface displaying a predetermined route for the event;
obtaining a real time position of the participant along the route using a position sensing device and performance data associated with the participant and the event, and displaying the position in association with the route displayed on the graphical map interface;
enabling the observer to generate an inquiry as to the elapsed time or time of arrival for the participant with respect to an arbitrary real time position of the observer at an intermediate point along the race route;
comparing the real time performance data for the participant to the route data and predicting the elapsed time or time of arrival at the real time position of the observer for the participant with respect to said inquiry; and
displaying the predicted elapsed time or time of arrival at the real time position of the observer for the participant on the display unit.

12. The portable device of claim 11, the program module effective when executed by the microprocessor to further direct the performance of enabling the observer to select a participant from a plurality of participants associated with the event via the graphical user interface.

13. The portable device of claim 12, the program module effective when executed by the microprocessor to further direct the performance of obtaining historical performance data associated with the selected participant and displaying the real time position of the participant relative to a corresponding position associated with the historical performance data.

14. The portable device of claim 12, the program module effective when executed by the microprocessor to further direct the performance of obtaining historical performance data associated with the selected participant and displaying real time performance metrics for the participant relative to corresponding performance metrics associated with the historical performance data.

15. The portable device of claim 12, the program module effective when executed by the microprocessor to further direct the performance of displaying the position of a first participant selected by the observer relative to corresponding positions associated with the real time performance data for additional selected participants.

16. The portable device of claim 12, the selected participant comprising an actual participant in the event, the program module effective when executed by the microprocessor to further direct the performance of:
obtaining historical performance data associated with one or more previous participants in the event and
displaying the position of the actual participant relative to corresponding positions associated with the historical performance data for the previous participants.

17. The portable device of claim 12, the selected participant comprising an actual participant in the event, the program module effective when executed by the microprocessor to further direct the performance of obtaining theoretical performance data associated with one or more virtual participants in the event and displaying the position of the actual participant relative to corresponding positions associated with the theoretical performance data for the virtual participants.

18. The portable device of claim 11, the performance data for the participant comprising positioning data obtained via a GPS system.

19. The portable device of claim 18, the performance data for the participant further comprising one or more of biometric measurement data and local equipment measurement data.

20. The portable device of claim 11, the program module effective when executed by the microprocessor to further direct the performance of comparing the performance data for the participant to predetermined benchmark values.

21. The portable device of claim 11, the program module effective when executed by the microprocessor to further direct the performance of:
transmitting a request for route data associated with an event selected by the observer via a communications network to a server having the route data stored thereon, and
receiving the route data from the server via the communications network.

22. A method comprising:
enabling user selection of an event having at least one participant via a graphical user interface on a display unit for a user computing device;
generating a graphical map interface on the display unit, the map interface displaying a predetermined route for the event;
obtaining a real time position of a participant along the route using a position sensing device and displaying the position in association with the route displayed on the graphical map interface;
enabling user inquiry as to a predicted intermediate location along the route for the participant based upon an observer-defined elapsed time or time of arrival;
comparing the real time performance data for the participant to the route data and predicting the location of the participant with respect to said defined elapsed time or time of arrival; and
displaying the predicted location of the participant with respect to said inquiry on the display unit of the user computing device.

* * * * *